United States Patent
Brandenburger et al.

(10) Patent No.: US 11,013,663 B2
(45) Date of Patent: May 25, 2021

(54) CONTAINER FOR A MEDICAL LIQUID

(71) Applicant: Fresenius Kabi Deutschland GmbH, Bad Homburg (DE)

(72) Inventors: Torsten Brandenburger, Reichelsheim (DE); Ismael Rahimy, Friedberg (DE); Christian Frensch, Hofheim (DE)

(73) Assignee: Fresenius Kabi Deutschland GmbH, Bad Homburg (DE)

(*) Notice: Subject to any disclaimer, the term of this patent is extended or adjusted under 35 U.S.C. 154(b) by 526 days.

(21) Appl. No.: 15/573,591

(22) PCT Filed: May 11, 2016

(86) PCT No.: PCT/EP2016/060539
§ 371 (c)(1),
(2) Date: Nov. 13, 2017

(87) PCT Pub. No.: WO2016/180869
PCT Pub. Date: Nov. 17, 2016

(65) Prior Publication Data
US 2019/0209435 A1     Jul. 11, 2019

(30) Foreign Application Priority Data

May 13, 2015  (EP) ................................. 15167619

(51) Int. Cl.
*A61J 1/20*     (2006.01)
*A61J 1/14*     (2006.01)
(Continued)

(52) U.S. Cl.
CPC ........... *A61J 1/2044* (2015.05); *A61J 1/1412* (2013.01); *A61J 1/2048* (2015.05);
(Continued)

(58) Field of Classification Search
CPC ...... A61J 1/1406; A61J 1/1475; A61J 1/2044; A61J 1/1481; A61J 1/2006; A61J 1/201;
(Continued)

(56) References Cited

U.S. PATENT DOCUMENTS

| | | | | |
|---|---|---|---|---|
| 4,809,679 A | * | 3/1989 | Shimonaka | A61B 1/00137 600/154 |
| 5,209,737 A | * | 5/1993 | Ritchart | A61B 17/3462 604/167.03 |

(Continued)

FOREIGN PATENT DOCUMENTS

| WO | WO2005/037362 | 4/2005 |
|---|---|---|
| WO | 2010/034470 A1 | 4/2010 |

(Continued)

OTHER PUBLICATIONS

Rubber Material Selection Guide NR or Natural Rubber Polyisoprene, Robinson Rubber Products Company, 2005.*

(Continued)

*Primary Examiner* — Adam Marcetich
(74) *Attorney, Agent, or Firm* — Occhiuti & Rohlicek LLP

(57) ABSTRACT

A container for a medical liquid, comprising a connection piece via which a medical liquid can be pumped into or out of the container, an attachment part which can be attached to the connection piece and connected to a pump device to pump a medical liquid or out of the container, and a sealing element for sealing a passage between the connection piece and the attachment part. The sealing element has a slot opening which is closed against a liquid flow when the pump device is not attached to the attachment part and which is open when the pump device is attached to the attachment part such that a medical liquid can be pumped through the slot opening. The attachment part has a connection portion with an opening into which the connection piece can be (Continued)

inserted along an insertion direction in order to connect to the attachment part.

21 Claims, 9 Drawing Sheets

(51) Int. Cl.
*A61M 39/20* (2006.01)
*A61M 39/26* (2006.01)
*A61M 39/04* (2006.01)
*A61M 39/10* (2006.01)
*A61M 39/24* (2006.01)

(52) U.S. Cl.
CPC .......... *A61M 39/045* (2013.01); *A61M 39/20* (2013.01); *A61M 39/26* (2013.01); *A61J 1/2096* (2013.01); *A61M 2039/1033* (2013.01); *A61M 2039/1061* (2013.01); *A61M 2039/1072* (2013.01); *A61M 2039/2426* (2013.01)

(58) Field of Classification Search
CPC ........ A61J 1/2013; A61J 1/202; A61J 1/2041; A61M 39/045; A61M 39/20; A61M 2039/1072
See application file for complete search history.

(56) References Cited

U.S. PATENT DOCUMENTS

| | | | | |
|---|---|---|---|---|
| 5,289,849 A * | 3/1994 | Paradis | ................. | A61M 39/04 137/606 |
| 5,797,897 A * | 8/1998 | Jepson | ................. | A61J 1/2089 604/239 |
| 5,961,497 A * | 10/1999 | Larkin | ................. | A61M 39/045 604/201 |
| 6,068,011 A * | 5/2000 | Paradis | ................. | A61M 39/02 137/1 |
| 6,165,168 A * | 12/2000 | Russo | ................. | A61M 39/045 604/247 |
| 6,712,202 B2 * | 3/2004 | Muller | ................. | A61J 1/2093 206/219 |
| 7,828,787 B2 * | 11/2010 | Brandenburger | ..... | A61J 1/1475 604/411 |
| 7,857,802 B2 * | 12/2010 | Brandenburger | ... | A61M 39/045 604/415 |
| 8,136,330 B2 * | 3/2012 | Ostler | ................. | A61J 1/10 53/111 R |
| 8,162,915 B2 * | 4/2012 | Brandenburger | ..... | A61M 39/20 604/415 |
| 9,108,031 B2 * | 8/2015 | Brandenburger | ..... | A61M 39/16 |
| 2001/0042850 A1 * | 11/2001 | Cote, Sr. | ................ | A61M 39/02 251/149.1 |
| 2002/0193752 A1 * | 12/2002 | Lynn | ..................... | A61M 39/26 604/249 |
| 2003/0139756 A1 * | 7/2003 | Brustad | ............... | A61B 17/3462 606/167 |
| 2003/0187420 A1 * | 10/2003 | Akerlund | ........... | A61M 5/1409 604/408 |
| 2003/0208165 A1 * | 11/2003 | Christensen | .......... | A61M 39/26 604/256 |
| 2005/0090713 A1 * | 4/2005 | Gonzales | ........... | A61M 39/0606 600/135 |
| 2005/0215943 A1 * | 9/2005 | Brandenburger | ..... | A61J 1/1475 604/30 |
| 2007/0060902 A1 * | 3/2007 | Brandenburger | ..... | A61M 39/26 604/403 |
| 2008/0108939 A1 * | 5/2008 | Moulton | ............ | A61M 39/045 604/43 |
| 2008/0132832 A1 * | 6/2008 | McKinnon | .......... | A61M 39/045 604/93.01 |
| 2010/0016826 A1 * | 1/2010 | Billiet-Prades | ....... | A61J 1/2089 604/416 |
| 2010/0312061 A1 * | 12/2010 | Hess | .................. | A61B 17/3423 600/201 |
| 2011/0166532 A1 * | 7/2011 | Brandenburger | ... | A61M 39/045 604/201 |
| 2014/0014547 A1 * | 1/2014 | Ogawa | .................. | A61J 1/2093 206/438 |
| 2014/0228775 A1 * | 8/2014 | Burkholz | ............ | A61M 39/162 604/244 |
| 2016/0001056 A1 * | 1/2016 | Nelson | ................. | A61M 39/26 604/247 |

FOREIGN PATENT DOCUMENTS

| | | |
|---|---|---|
| WO | WO2013/017698 | 2/2013 |
| WO | WO2015/007703 | 1/2015 |

OTHER PUBLICATIONS

Definition of Play at Dictionary.com. https://www.dictionary.com/browse/play?s=ts. Accessed Oct. 7, 2020.*

* cited by examiner

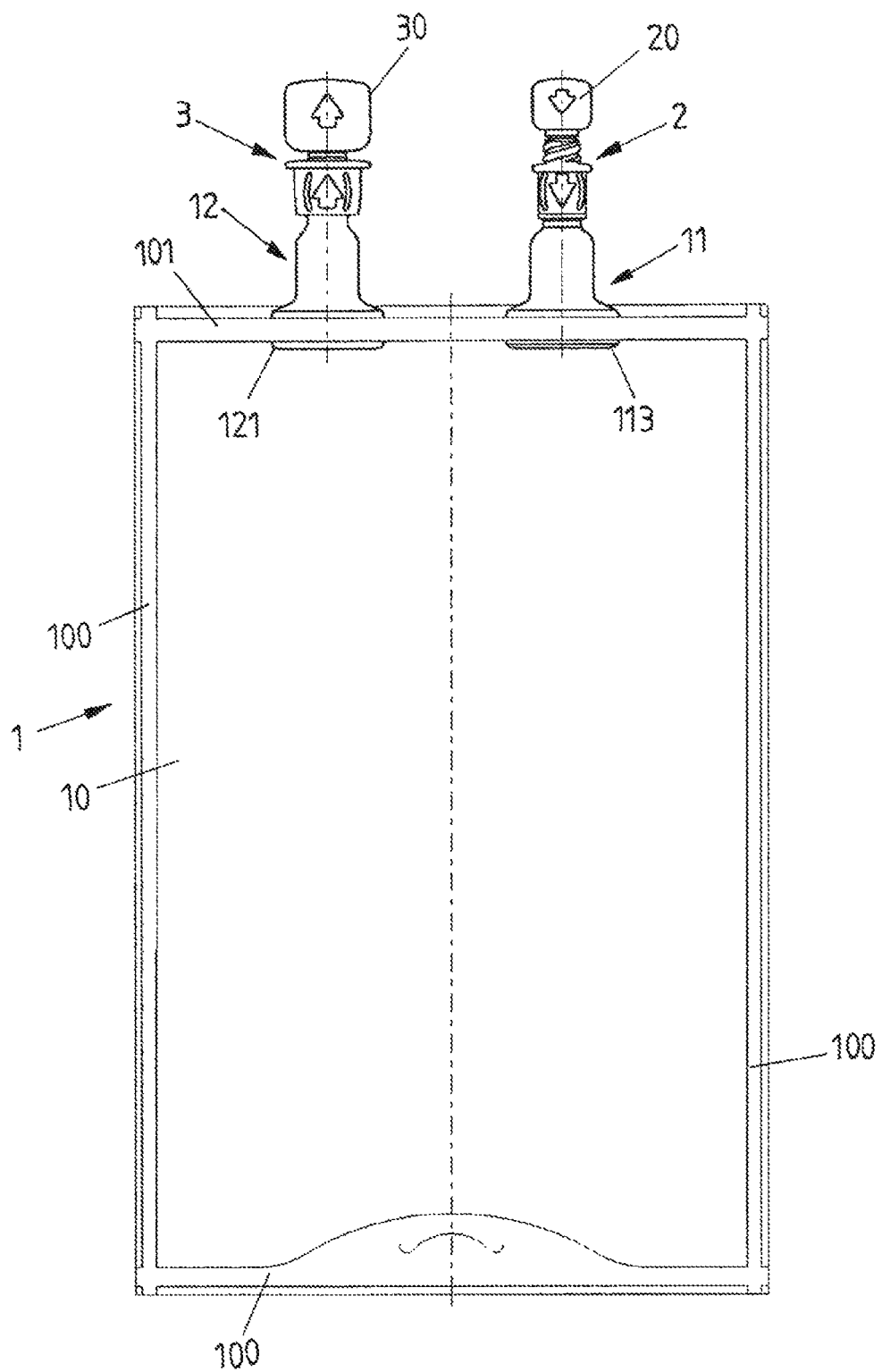

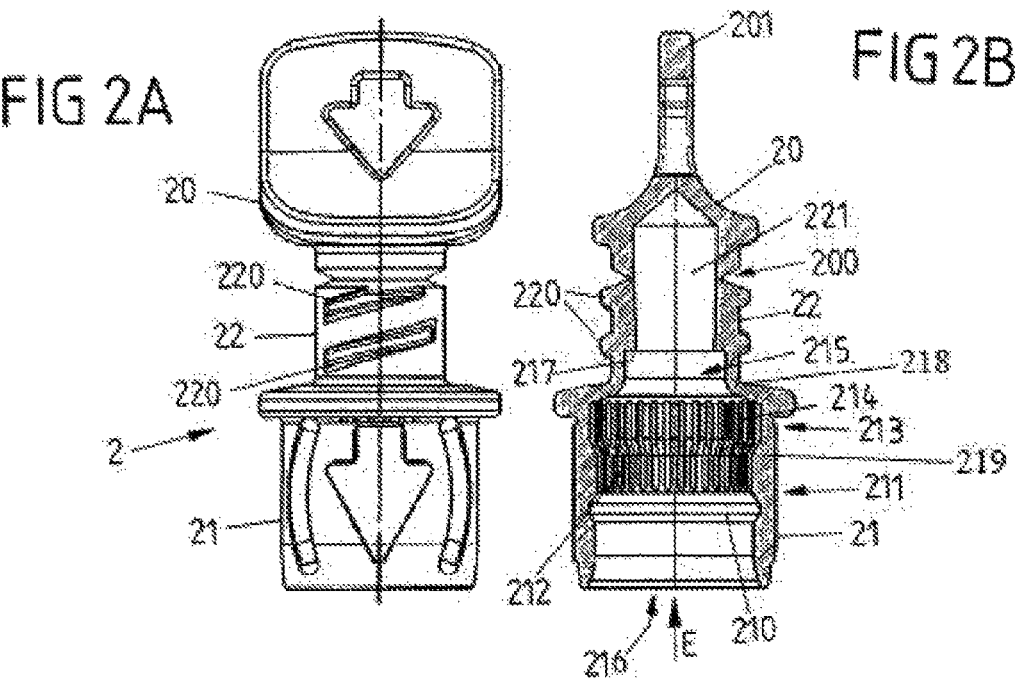
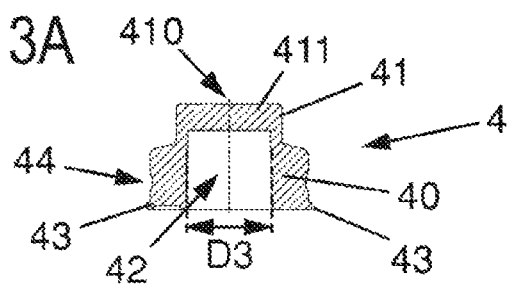
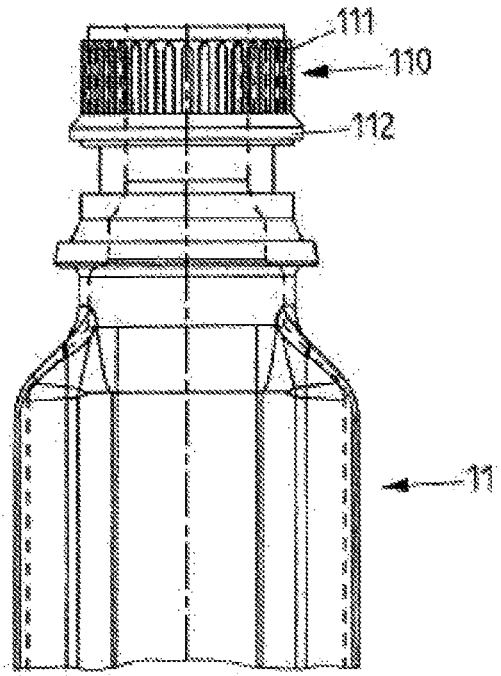

CONTAINER FOR A MEDICAL LIQUID

CROSS REFERENCE TO RELATED APPLICATIONS

This application is the national phase under 35 USC 371 of international application no. PCT/EP2016/060539, filed May 11, 2016, which claims the benefit of the priority date of European application no. 15167619.4 filed May 13, 2015. The contents of the aforementioned applications are incorporated herein in their entirety.

The invention relates to a container for a medical liquid according to the preamble of claim 1.

A container of this type includes one or multiple connection pieces, by means of which a medical liquid can be conveyed into the container or out of the container. An attachment part, which can be connected to a conveying device, e.g. a syringe, for conveying a medical liquid into the container or out of the container, can be attached to at least one of said connection pieces. A sealing element seals a transition between the connection piece and the attachment part, the sealing element generally comprising a slot opening which, with the conveying device not attached to the attachment part, is closed against a passage of liquid and, as a result of attaching the conveying device to the attachment part, can be opened in such a manner that a medical liquid can be conveyed through the slot opening.

Such a container can be configured, for example, as a flexible pouch or also as an ampoule or another bottle container.

In the case of a connector disclosed in WO 2005/037362 A1, a self-sealing diaphragm is inserted into a duct-shaped recess of a connection part for a packaging containing a medical liquid. The duct-shaped recess is closed by a break-off part which can be broken off from the connection part to release the duct-shaped recess such that a syringe can be attached to the connection part with the connecting piece. As a result of attaching the syringe to the connection part, the diaphragm is able to be opened such that a liquid can be conveyed into a container or out of the container. WO 2015/007703 A1 describes a corresponding ampoule for a medical liquid.

In the case of a connector disclosed in WO 2010/034470 A1, a hollow body with a tip is arranged on one side of a diaphragm which is remote from a syringe to be attached to the diaphragm. When the syringe is attached to the connector, the syringe presses the diaphragm onto the tip of the hollow body such that the syringe engages the hollow body and consequently a flow through the diaphragm is made possible.

WO 2013/017698 A1 describes a needle-free connector. Said needle-free connector includes a valve body with a first and a second opening. A hollow elastic diaphragm is arranged in the valve body. The diaphragm has a first and a second end. The diaphragm comprises a side wall which connects the first end to the second end. The side wall of the diaphragm abuts against an inner surface of the valve body.

It is the object of the present invention to provide a container with a connection piece and an attachment part which is attachable thereto, where a large flow, in particular with a small amount of effort expended, can be obtained for conveying a medical liquid into the container or out of the container.

Said object is achieved by the subject matter with the features of claim 1.

Claim 1 describes a container for a medical liquid, having a connection piece, by means of which a medical liquid is conveyable into the container or out of the container, an attachment part which is attachable to the connection piece and is connectable to a conveying device for conveying a medical liquid into the container or out of the container, and a sealing element for sealing a transition between the connection piece and the attachment part, wherein the sealing element comprises a slot opening which, with the conveying device not attached to the attachment part, is closed against a passage of liquid and, as a result of attaching the conveying device to the attachment part, is to be opened in such a manner that a medical liquid is conveyable through the slot opening. The attachment part comprises a connecting portion with an opening into which the connection piece is insertable along an insertion direction (E) for connection to the attachment part. The opening comprises a first receiving portion and a second receiving portion which connects axially thereto along the insertion direction (E), wherein, with the attachment part attached to the connection piece, the first receiving portion receives a head of the connection piece and the second receiving portion receives a portion of the sealing element.

According to the invention, the first receiving portion comprises a first diameter D1 and the second receiving portion comprises a second diameter D2, wherein the first diameter D1 is smaller than the second diameter D2 and the sealing element, with the conveying device not attached to the attachment part, is received in or on the second receiving portion with radial play. This makes it possible for the sealing element to be able to be inserted in the second receiving portion with play and nevertheless, at the same time, to be able to be held in a clamping manner between the connection part and the attachment part. Because the sealing element is inserted with play in the second receiving portion, when a conveying device is attached, in particular a syringe, it can be deformed radially and consequently can be urged aside by the conveying device such that the slot opening provided in the sealing element can be opened in a reliable manner as the sealing element is deformed and can be exposed, preferably completely.

In one embodiment, it is provided in the case of the container that the sealing element is produced from a thermoplastic elastomer. In particular, the thermoplastic elastomer (TPE) comprises, in this connection, a Shore Hardness A of between 25 and 70, preferably of between 50 and 60. The thermoplastic elastomer preferably is or includes a TPE material of the styrene TPE type.

The named Shore Hardness is a material characteristic for thermoplastic elastomers which is fixed in standard DIN ISO 7619-1. In a Shore Hardness test, a spring-loaded pin produced from hardened steel is fitted onto a material to be tested and the penetration depth into the material is tested. A high Shore Hardness means that the material has a greater degree of hardness. In general, the Shore Hardness is measured on a scale of between 0 and 100. The tip of the steel pin presses into the material at Shore A or penetrates the material at Shore D. The depth of impression/penetration is measured on a scale of 0-100. The steel pin has either the geometry of a truncated cone (Shore A) or of a needle tip (Shore D).

In the case of conventional containers, there can be the problem of the sealing element, for example in the form of a diaphragm, not opening completely when a conveying device, in particular a syringe, is attached. This can make it necessary to re-attach the conveying device or, however, can impair the flow through the connection piece. An additional hollow body with a tip, which is to support the opening of the diaphragm, is provided for this purpose in the prior art.

In the case of the connector according to the invention, however, no additional hollow body is provided. Whilst conventional sealing elements can be produced from a comparatively soft material, the sealing element in one embodiment is produced from a thermoplastic elastomer, preferably with a comparatively high Shore Hardness. In an alternative embodiment, the sealing element is produced from polyisoprene.

In one embodiment, the sealing element is provided in such a manner that when a conveying device, in particular a syringe, is attached to the attachment part, the sealing element can be deformed sufficiently to open the slot opening and exposes a sufficiently large flow opening. The conveying device, when it is attached to the attachment piece, extends, preferably with a connecting piece, through the slot opening of the sealing element such that a flow between the conveying device and the container can be effected unobstructed by the sealing element. In one embodiment, at least 80%, preferably at least 90%, of the opening cross section in the conveying device, through which the liquid is transported, is exposed and consequently not covered by the seal. Preferably the entire cross section of the opening in the conveying device, through which the liquid is transported, is exposed.

For example, a higher degree of hardness of the sealing element can enable an advantageous flow because the sealing element with a higher degree of hardness—in particular compared to a softer sealing element—can be deformed advantageously to open the slot opening when the conveying device, in particular a connecting piece of a syringe, is attached. In particular, the sealing element can be urged aside radially without excessive deformation occurring in the axial direction and, in particular, the sealing element cannot stretch excessively in the axial direction when the conveying device is attached.

According to the invention, the attachment part comprises a connecting portion with an opening into which the connection piece can be inserted along an insertion direction for connection to the attachment part. As a result of inserting the connection piece into the opening of the attachment part, the connection piece is connected to the attachment part in a positive locking manner, the sealing element resting in a clamping manner between the attachment part and the connection piece and consequently being held in a sealing manner between the attachment part and the connection piece.

The basic form of the opening can be substantially cylindrical. A first receiving portion is realized in the opening in this connection, to which—when viewed along the insertion direction—a second receiving portion is axially connected. If the attachment part is attached to the connection piece, the first receiving portion thus receives a head of the connection piece, preferably in a positive locking manner, whilst a, for example, rotationally symmetrical body of the sealing element rests in the second receiving portion.

In this connection, the diameter of the first receiving portion is smaller than that of the second receiving portion. This makes it possible for the sealing element to be inserted with play in the second receiving portion and nevertheless, at the same time, to be able to be held in a clamping manner between the connection part and the attachment part. Because the sealing element is inserted with play in the second receiving portion, when a conveying device is attached, in particular a syringe, it can be deformed radially and consequently can be urged aside by the conveying device such that the slot opening provided in the sealing element can be opened in a reliable manner as the sealing element is deformed.

The attachment part and the connection piece are connected together in a positive locking manner by means of the first receiving portion. In this connection, an inner toothing which extends around the insertion direction can be provided on the first receiving portion, said inner toothing, with the attachment part attached to the connection piece, engages an assigned toothing on the head of the connection piece in a positive locking manner such that the attachment part and the connection piece are fixed with respect to one another so as to be non-rotatable about the insertion direction. Once the attachment part has been attached to the connection piece, the attachment part and the connection piece can consequently (no longer) be rotated with respect to one another such that the attachment part is fixed on the connection piece.

In one embodiment, both the first receiving portion and the second receiving portion comprise a toothing, for example in the form of a circumferential inner toothing. The toothing of the first receiving portion serves for the non-rotatable fixing on the head of the connection piece. The toothing of the second receiving portion serves for removing the attachment part from the mold in an improved manner after the injection molding process during production.

In an advantageous configuration, the sealing element comprises a cylindrical body, which, when the attachment part is attached to the connection part, is held in a clamping manner between the connection piece and the attachment part, and a sealing head which connects to the body and in which the slot opening is realized. In this connection, the body can comprise a larger diameter than the sealing head (when viewed radially to the insertion direction). The sealing element is preferably configured overall in a rotationally symmetrical manner with a cylindrical body and a sealing head which connects thereto.

The sealing head is preferably realized in a flat manner on a side remote from the body. This makes it possible, when a conveying device, in particular a syringe, is attached to the attachment part, for the sealing head to be able to be urged aside in an advantageous manner as a result of inserting a connecting piece of the conveying device into the slot opening such that, with the conveying device attached completely to the attachment part, the connecting piece penetrates the sealing head of the sealing element and consequently a flow between the conveying device and the container is not impaired by the sealing element.

However, it is also conceivable and possible for the sealing head to be curved convexly outward or concavely inward on its side remote from the body.

The body of the sealing element preferably comprises a, preferably cylindrical or substantially cylindrical, bore which is delimited axially by the sealing head and is preferably realized with a constant diameter over its entire height (when viewed along the insertion direction) or is tapered toward the sealing head. By the, preferably cylindrical, bore being realized with a large diameter—compared to a flow opening of a connecting piece of a conveying device—it can be ensured that the sealing element does not obstruct a flow with its body when the conveying device is attached to the attachment part.

In order to facilitate the attaching of the attachment part to the connection piece, a positive locking element, which protrudes radially from the body, for example in the form of a circumferential annulus, can be provided on the sealing element, which positive locking element serves for the purpose of holding the sealing element on the attachment part when it is inserted into the opening of the attachment part. The mounting of the attachment part on the connection piece can consequently be effected together with the sealing element, which is inserted into the opening of the attachment part, without particular provisions having to be made to hold the sealing element in position with respect to the attachment part.

In an advantageous configuration, the attachment part comprises a threaded portion with at least one thread for producing a threaded connection to a conveying device which is to be attached to the attachment part. The threaded portion can provide, for example, a Luer attachment, by means of which the closure part can be connected in the manner of a so-called Luer lock to a conveying device, for example a syringe. To this end, the conveying device can comprise a connection element in the form of a union nut with an internal thread which can be moved into threaded engagement with the threaded portion such that the conveying device can be releasably connected to the container by means of the threaded portion.

A break-off piece which, in a state connected to the threaded portion, closes an opening of the threaded portion and to expose the opening can be removed, in particular manually broken off, from the threaded portion, preferably connects to the threaded portion—in an initial state prior to attaching a conveying device to the attachment part. The attachment part is closed in its initial state by means of the break-off piece such that the access to the container, provided by means of the connection piece, is securely sealed. To open it, the break-off piece can be removed, in particular broken off, from the threaded portion, it being possible to provide, to this end, a defined predetermined breaking point between the break-off piece and the threaded portion, at which the break-off piece can be separated in a defined manner from the threaded portion. With the break-off piece broken off, the opening of the threaded portion is then exposed such that a conveying device can be attached to the attachment part for conveying a liquid in or out. The interior of the attachment part, which is closed by the break-off piece, is preferably already sterile in the initial state in which the break-off piece has not yet been removed.

A connector, in particular for an embodiment of the previously described container, is also within the field of the invention. The connector includes a connection piece, by means of which a medical liquid is conveyable, an attachment part which is connected to the connection piece, preferably by means of attachment, and is connectable to a conveying device for conveying a medical liquid through the connection piece, and a sealing element for sealing a transition between the connection piece and the attachment part. The sealing element comprises a slot opening which, with the conveying device not attached to the attachment part, is closed against a passage of liquid and, as a result of attaching the conveying device to the attachment part, is to be opened in such a manner that a medical liquid is conveyable through the slot opening. The attachment part comprises a connecting portion with an opening into which the connection piece is insertable along an insertion direction (E) for connection to the attachment part. The opening comprises a first receiving portion and a second receiving portion which connects axially thereto along the insertion direction (E). With the attachment part attached to the connection piece, the first receiving portion receives a head of the connection piece and the second receiving portion receives a portion of the sealing element. The connector is characterized in that the first receiving portion comprises a first diameter D1 and the second receiving portion comprises a second diameter D2, wherein the first diameter D1 is smaller than the second diameter D2 and the sealing element, with the conveying device not attached to the attachment part, is received in the second receiving portion with radial play. In one configuration, the sealing element is produced from a thermoplastic elastomer. For possible further embodiments of the connector, reference is made to the previous description.

In addition, a sealing element for an embodiment of the previously described container and/or of the previously described connector is also within the field of the invention. Said sealing element is characterized in that it comprises a body with an outer diameter of between 6 mm and 10 mm and a sealing head, which connects to the body, with an outer diameter of between 4 mm and 7 mm. In one configuration, the sealing element is produced from a thermoplastic elastomer. For possible further embodiments of the sealing element, reference is made to the previous description.

In the case of an arrangement of a container according to the previously described type and of a conveying device, the conveying device can be attached to the attachment part, which is connected to the connection piece, by way of a connecting piece. In this connection, the connecting piece moves into contact with the sealing element inside the attachment part and urges the sealing element aside in such a manner that, with the conveying device attached, the connecting piece penetrates the slot opening of the sealing element, preferably completely, and consequently a flow between the conveying device and the container is not impaired or is not substantially impaired by the sealing element.

The sealing element can comprise, for example, an outer diameter of between 6 mm and 10 mm, preferably of between 7 mm and 9 mm, for example of 8 mm, corresponding to the outer diameter of the body of the sealing element.

The diameter of the sealing head of the sealing body which connects to the body can, in contrast, be between 4 mm and 7 mm, for example between 4.5 mm and 5.5 mm, in particular 5.1 mm.

The overall height of the sealing element can be, for example, between 4 mm and 7 mm, for example between 4.5 mm and 6 mm, in particular 5.1 mm.

The inner bore of the sealing element can comprise, for example, a diameter of between 3.5 mm and 5 mm, for example of 4.2 mm, and an axial height of between 2.5 mm and 5 mm, for example of between 3.5 mm and 4 mm, in particular of 3.8 mm.

The attachment part can comprise on the connecting portion, for example, an outer diameter of between 9 mm and 13 mm, for example of between 10 mm and 11 mm, in particular of 10.2 mm.

The attachment part can comprise, in particular when used on a container, an overall height (with connected break-off piece) of between 20 mm and 40 mm, for example of between 25 mm and 35 mm, in particular of between 28 mm and 30 mm.

The connection piece, in contrast, can comprise, on its head, which is to be inserted into the connecting portion of the attachment part, for example a diameter of between 7 mm and 12 mm, for example of between 8 and 10 mm.

The overall height of the connection piece can be, for example, between 30 mm and 50 mm, for example between 35 mm and 45 mm, in particular between 38 mm and 40 mm.

The concept underlying the invention is to be explained in more detail below by way of the exemplary embodiments shown in the figures, in which:

FIG. 1 shows a view of a container in the form of a pouch having connection pieces which are provided thereon and are closed by attachment parts;

FIG. 2A shows a side view of an attachment part;

FIG. 2B shows a sectioned view through the attachment part according to FIG. 2A;

FIG. 3A shows a sectioned view through a sealing element which is to be attached to the attachment part;

FIG. 4 shows a side view of a connection piece, to which the attachment part is to be attached;

Figure 3B:
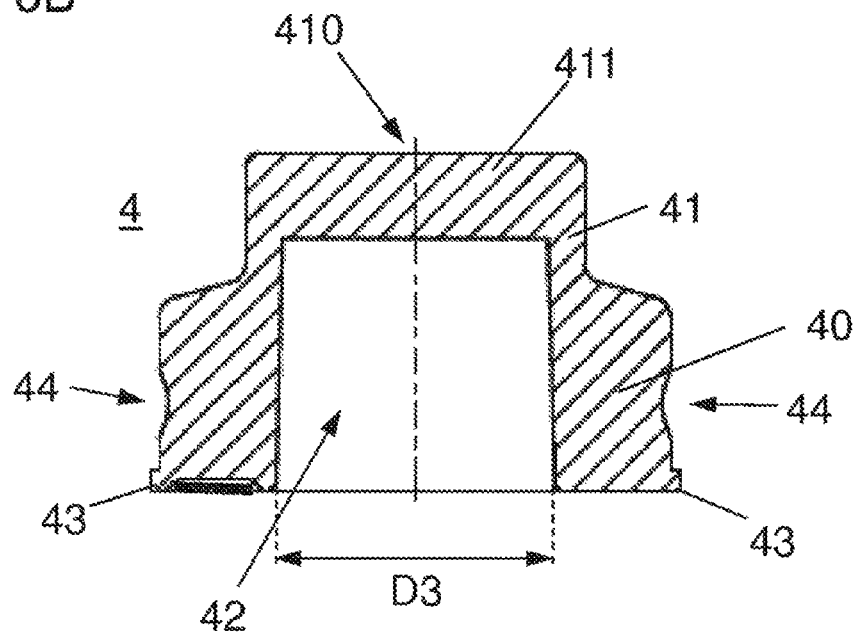
FIG. 3B shows an enlarged view of the sectioned view from FIG. 3A.

FIG. 1 shows a schematic view of a container 1 in the form of a flexible pouch for storing a medical liquid, for example a medication, a saline solution, a nutrient solution for enteral or parenteral nutrition or the like. The pouch 1 includes a pouch body 10 which is realized for receiving the medical liquid and in a manner known per se encloses a volume into which a medical liquid can be filled or from which the medical liquid can be removed.

It must be pointed out at this juncture that the present invention is not restricted to a flexible pouch, but can be applied, in principle, to very different containers 1, in particular also ampoules or other bottles for storing medical liquids.

The container 1 includes two connection pieces 11, 12, which provide the two access points into the interior of the container 1. A first connection piece 11 is provided, in this connection, in particular, to feed a medical liquid into the container 1, whilst a second connection piece 12 serves for removing liquid out of the interior of the container 1.

In the case of the exemplary embodiment shown, attachment parts 2, 3 in the form of caps are attached to both connection pieces 11, 12. The connection pieces 11, 12 are closed in a liquid-tight manner to the outside by means of the attachment parts 2, 3 such that no liquid is able to pass out of the container 1 and the container 1 is sealed to the outside against ingress of dirt or the like.

Each attachment part 2, 3 comprises a break-off piece 20, 30 as a tamper-evident closure which can be broken off in order to gain access to the container 1.

Figure 7:
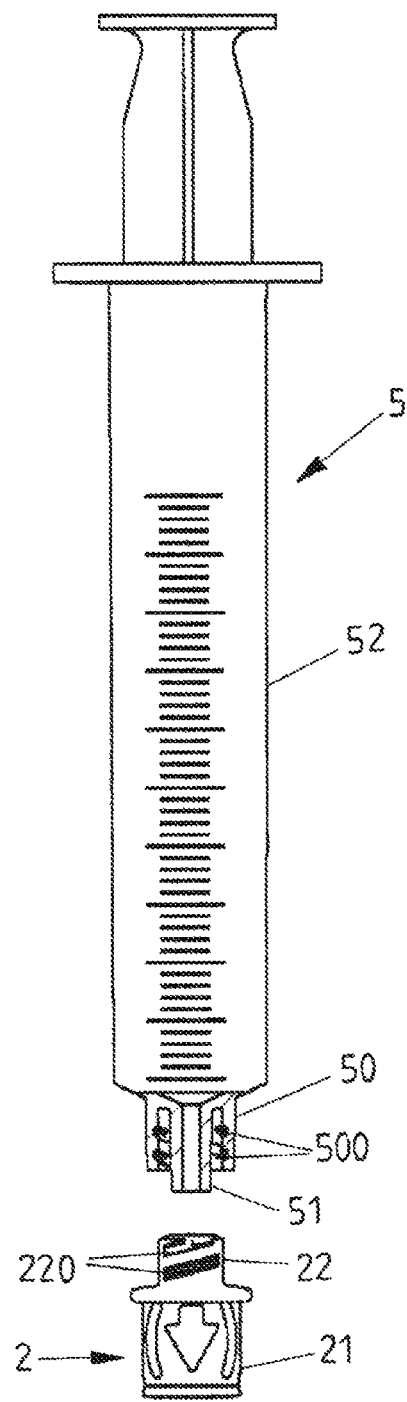
FIG. 7 shows a view of a conveying device prior to attachment to a threaded portion of an attachment part.

Whilst the attachment part 3, which is attached to the second connection piece 12, is configured for the attachment of a conveying device which comprises a mandrel in order to gain access to the container 1 by piercing a sealing element by means of the mandrel and to convey liquid out of the container 1, the first connection piece 11 and the attachment part 2 attached thereto provide so-called needle-free access, by means of which feeding liquid into the container 1 or liquid out of the container 1 can be performed without a needle using a conveying device 5 (see FIG. 7).

The container shown in FIG. 1 consists—in a manner known per se—of flexible foils which are welded together along weld seams 100, 101. The connection pieces 11, 12 each comprise in particular a boat form (so-called ship shape) and are each inserted with a widened portion 113, 121 between the foils of the container 1 and are welded with the foils in a liquid-tight manner by means of an upper weld seam 101. Consequently, two access points to the container 1 are created by means of the connection pieces 11, 12, by means of which liquid can be filled into the container 1 or can be removed out of the container 1.

An exemplary embodiment of a connector with a connection piece 11, an attachment part 2 and a sealing element 4 which, with the attachment part 2 attached to the connection piece 11, rests between the attachment part 2 and the connection piece 11, are shown in FIGS. 2A, 2B to 6.

The attachment part 2 includes a connecting portion 21, the basic form of which is cylindrical, to which a threaded portion 22 connects, the basic form of which is also cylindrical. The break-off piece 20 is connected integrally to the threaded portion 22, which carries threads 220 on its outer cylindrical shell surface, a predetermined breaking point 200, which enables a defined separation of the break-off piece 20 from the threaded portion 22 along the predetermined breaking point 200, being realized between the break-off piece 20 and the threaded portion 22.

The attachment part 2 is formed integrally, for example from plastics material by means of plastics material injection molding.

An inner opening 216, to which a conical opening 221, which penetrates the threaded portion 22, is connected, is realized in the connecting portion 21, the basic form of which is cylindrical. The diameter of the opening 221 is tapered in the direction of the inner opening 216.

The attachment part 2 can be attached to a head 110 of the connection piece 11. This is effected by the connection piece 11 being inserted with its head 110 into the opening 216 in an insertion direction E until a positive locking element in the form of a circumferential ring projection 112 on the head 110 moves into engagement in a positive locking manner with a latching engagement 210 in the form of a groove-shaped indentation inside the opening 216.

A first receiving portion 211 connects to the groove-shaped indentation 210 inside the opening 216 in the insertion direction E. A second receiving portion 213, which is continued in the direction of the threaded portion 22 by a third receiving portion 215, connects, in turn, to said first receiving portion 211. In a state in which the attachment part 2 is attached to the head 110 of the connection piece 11, the positive locking element 112, in the form of the circumferential ring projection, engages the latching engagement 210, in the form of the groove-shaped indentation, inside the opening 216 in a positive locking manner. In said state, the head 110, by means of a toothing 111 in the form of an outer toothing, additionally engages a toothing 212 in the form of an inner toothing on the first receiving portion 211. The attachment part 2 is consequently fixed in relation to the connection piece 11 both axially along the insertion direction E and non-rotatably about the insertion direction E such that the attachment part 2 is held on the connection piece 11 in a stationary manner.

Figure 5:
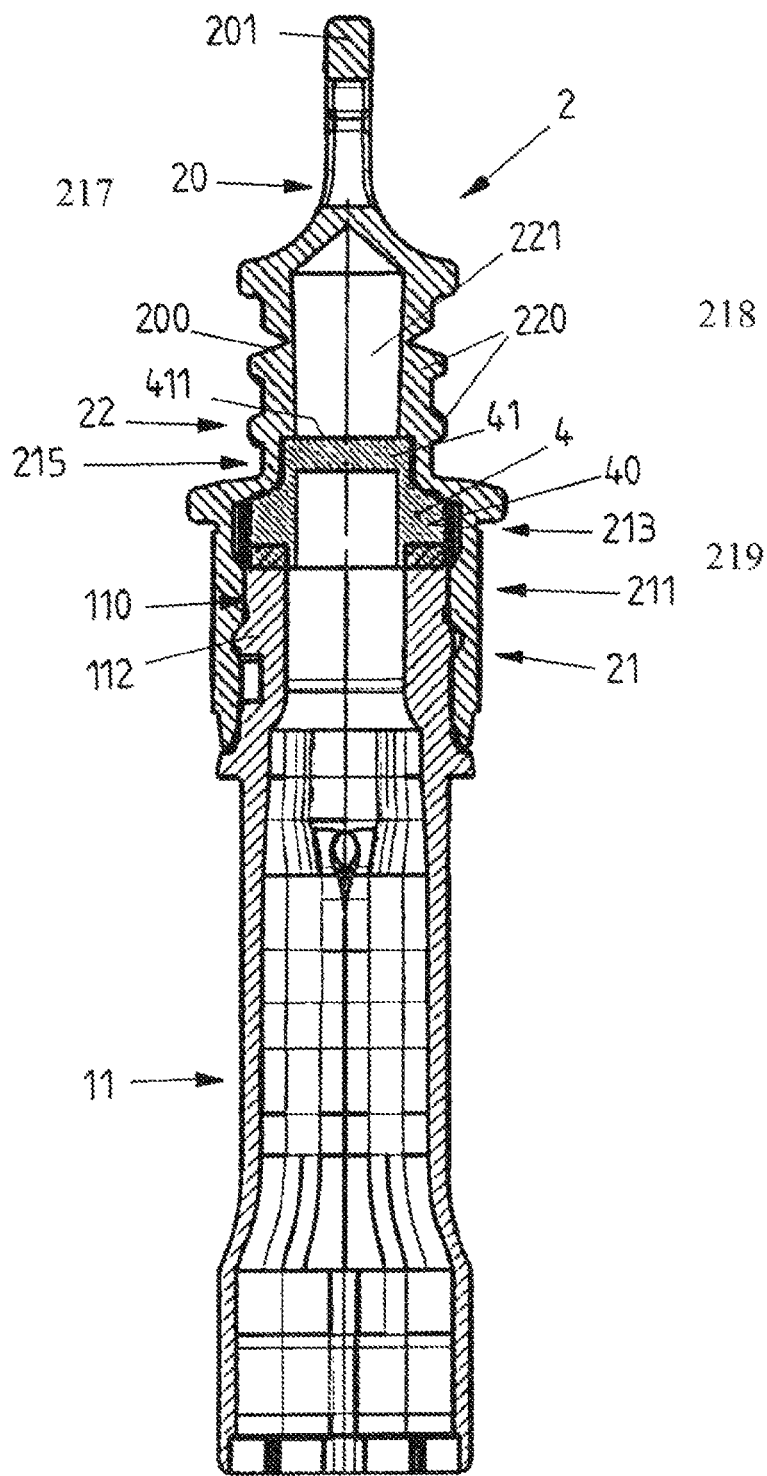
FIG. 5 shows a sectioned view through the attachment part and the connection piece in a state attached to one another.

In said attached state, the sealing element 4 lies between the attachment part 2 and the connection piece 11, as is shown in FIG. 5. The sealing element 4 comprises a rotationally symmetrical or a substantially rotationally symmetrical form. It is formed by a substantially cylindrical body 40, to which a sealing head 41 connects in the insertion direction E. A cylindrical bore 42 with a constant diameter D3 or a form that tapers slightly toward the sealing head 41 and is closed in a sealing manner in the insertion direction E by the sealing head 41, is realized in the body 40 (see for example FIGS. 3A and 3.B).

The sealing element 4 realizes a self-sealing diaphragm. Thus, arranged in the sealing head 41 is a slot opening 410 which penetrates the sealing head 41 axially and consequently—when a connecting piece 51 of a conveying device 5 is attached (see FIG. 7)—opens the sealing element 4, but is closed, however, when the conveying device 5 is not attached and consequently provides a liquid-tight transition between the attachment part 2 and the connection piece 11. The top side of the sealing element 4 is situated in the interior of the opening 221. It lies beneath the predetermined breaking point 200 and is consequently not flush with the top side of the opening 221.

In the state attached together, the sealing element 4 rests with its body 40 in the region of the second receiving portion 213 inside the opening 216 of the connecting portion 21, as is shown in FIG. 5. The body 40, in this case, is inserted with radial play in the second receiving portion 213 such that, with the conveying device 5 not attached, the cylindrical body 40 does not contact the extensive outer wall of the second receiving portion 213.

The second receiving portion 213 comprises a diameter D2 which is greater than the diameter D1 of the first receiving portion 211. The sealing element 4 is inserted with its body 40 consequently with radial play in the second receiving portion 213. A third step 219 is formed as a result between the first receiving portion 211 and the second receiving portion 213. Space to deform the sealing element 4 is created in this way such that the sealing element 4 can be urged aside in a favorable manner when a conveying device 5 is attached to the attachment part 2. The second receiving portion 213 preferably has a diameter D2 which is greater than the diameter D1 of the first receiving portion 211 by between 0.2 mm and 1.5 mm.

The sealing head 41, in this connection, rests in the third receiving portion 215 and in this way, as a result of abutment against a first step 217 of said third receiving portion 215, produces a sealing transition toward the attachment part 2. In addition, the sealing head 41 and the sealing body 40 abut against a second step 218.

In the state attached to one another, the sealing element 4 rests in a clamping manner between the attachment part 2 and the connection piece 11. The sealing head 41, in this connection, provides a liquid-tight separation between the conical opening 221 of the threaded portion 22 and the connection piece 11. The conical opening 221 for receiving a conical connecting piece 51, for example of a conveying device 5, preferably of a Luer syringe or a Luer Lock syringe, is arranged above the sealing element 4.

As can be seen in particular from FIG. 2, both the first receiving portion 211 and the second receiving portion 213 comprise a toothing 212, 214 in the form of a circumferential inner toothing. Whilst the toothing 212 of the first receiving portion 211 serves for fixing it non-rotatably on the head 110 of the connection piece 11, the toothing 214 of the second receiving portion 213 has no direct function in subsequent use. The toothing 214 of the second receiving portion 213 serves for removing the attachment part 2 out of the mold in an improved manner after the plastics material injection molding process. In the case of said removal from the mold, the attachment part 2 is withdrawn from a mold after the injection molding process. In order, in this connection, to prevent, during the withdrawal, a mandrel of the mold, which projects into the attachment part 2 and predetermines the form of the opening 216 of the mold, from damaging the toothing 212 on the first receiving portion 211 (which could not be excluded on account of the enlarged diameter of the second receiving portion 213), said mandrel also comprises a toothing in the region of the second receiving portion 213 (which is also correspondingly integrally molded on the second receiving portion 213). Because, during removal from the mold, a toothing portion of the mandrel which is complementary to the second receiving portion 213 is consequently pulled out of the attachment part 2 and said toothing portion slips through the toothing 212 of the first receiving portion 211, damage to the toothing 212 of the first receiving portion 211 can be reliably countered during removal from the mold.

The sealing element 4 comprises, on a side 411 of the sealing head 41 remote from the body 40, a flat form. The sealing head 41 is consequently not formed in a concave manner, as has been usual up to now, but is plane on its side 411 that faces the threaded portion 22, which facilitates the attachment of the conveying device 5 and the opening of the slot opening 410 during the attachment process.

Figure 3C:
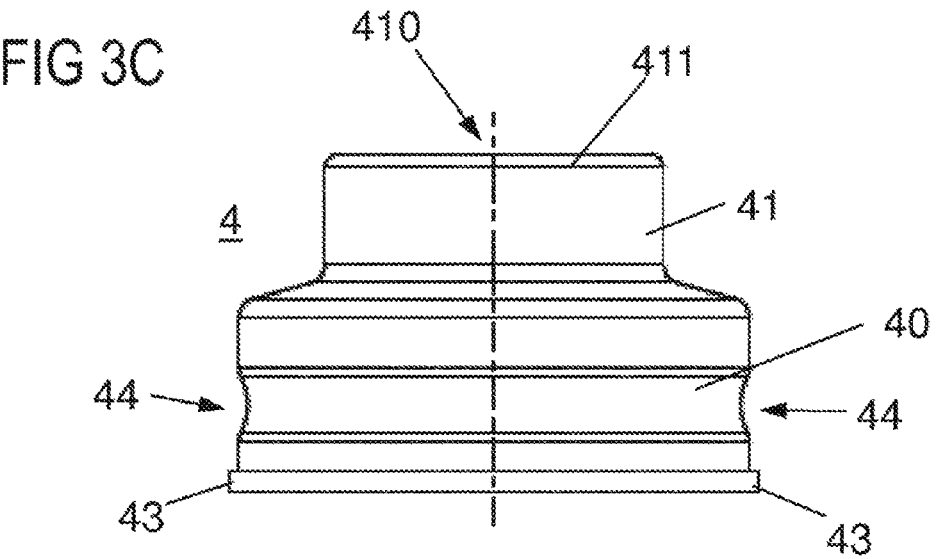
FIG. 3C shows an outside view of the sealing element which is to be attached to the attachment part.

The sealing element 4, as shown in FIGS. 3A to 3C, comprises on its body 40 a positive locking element 43 in the form of a circumferential annulus which serves for the purpose of holding the sealing element 4, once inserted into the opening 216, in a positive locking manner on the attachment part 2 such that the sealing element 4 cannot fall out of the opening 216. This facilitates the attachment of the attachment part 2 to the assigned connection piece 11. In particular, the attachment part 2 can be attached to the connection piece 11 with the sealing element 4 mounted on the attachment part 2 without the sealing element 4 having to be held manually in position on the attachment part 2. In addition, there is a, preferably circumferential, groove 44 on the outside of the sealing element 4. In detail, the groove 44 is arranged on the outside of the sealing body 40. The production of the sealing element 4, for example, can be supported as a result. The portions of the sealing body 40, which are situated above and below the groove 44, are substantially cylindrical in this case.

Figure 6:
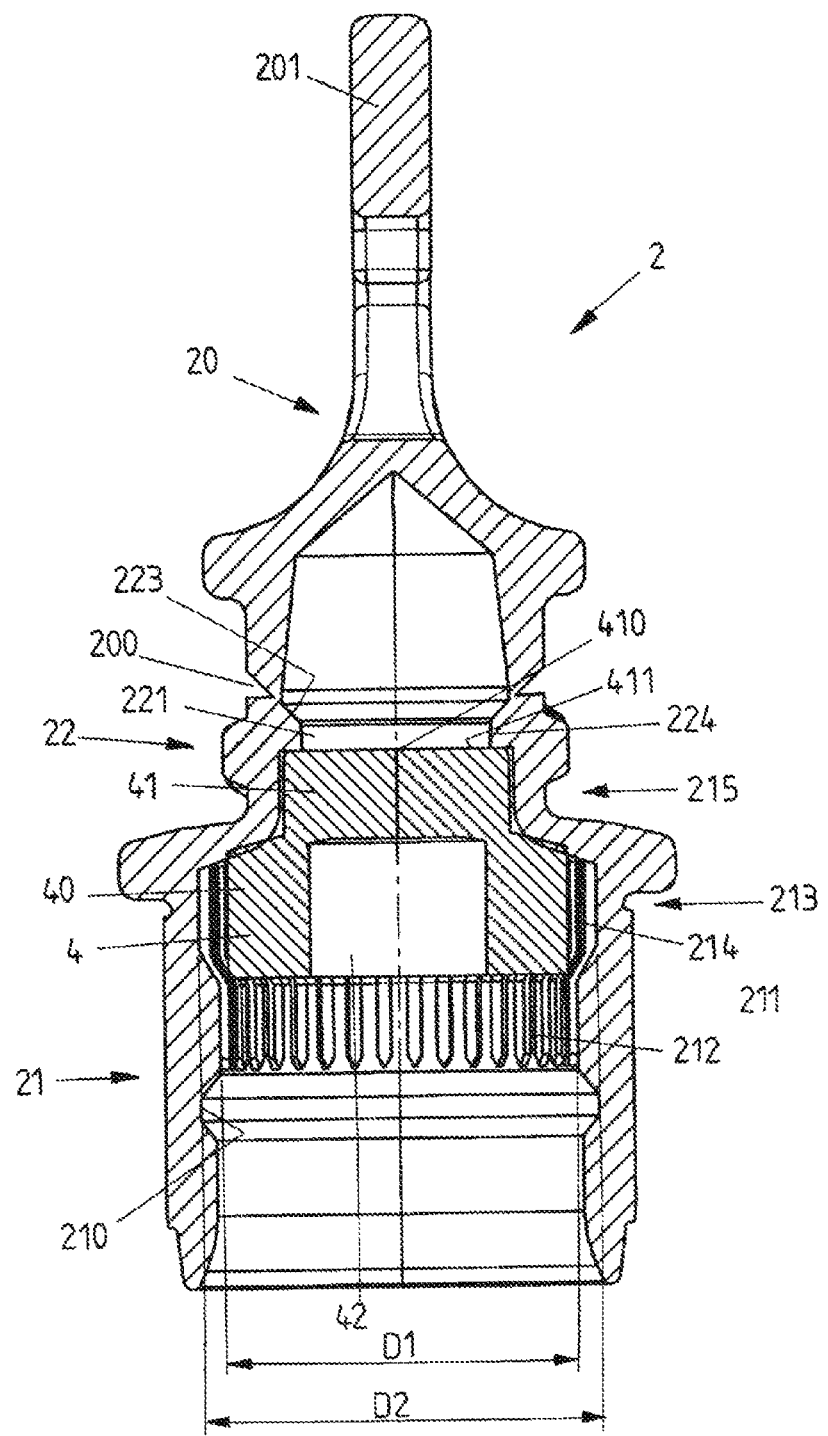
FIG. 6 shows a sectioned view through a different exemplary embodiment of an attachment part.

Another exemplary embodiment of a connector with an attachment part 2 is shown in FIG. 6. In the case of the exemplary embodiment according to FIG. 6, on the inside of the opening 221 of the threaded portion is realized a projection 224, which extends around the opening 221, projects radially inward into the opening 221 and forms a step against which the sealing element 4 abuts with its outwardly pointing top side 411. On the side remote from the top side 411, the projection 224 comprises a lead-in chamfer 223 which facilitates insertion of a connecting piece of a conveying device and engagement in the slot opening 410 of the sealing element. The attachment part 2 according to FIG. 6, as regards its operation, is otherwise substantially identical to the attachment part 2 of the exemplary embodiment according to FIGS. 2A, 2B to 5 such that reference is to be made entirely to what has been previously described.

A conveying device 5 is attached to the attachment part 2 as shown in FIG. 7. To attach the conveying device 5 to the attachment part 2, first of all the break-off piece 20 on a grip element 201, which is provided for this purpose, is gripped between two fingers and separated from the threaded portion 22 of the attachment part 2 at its predetermined breaking point 200. Once the break-off piece 20 has been broken off, the opening 221 inside the threaded portion 22 is exposed such that the conveying device 5 can be inserted, preferably in a sealing manner, into the opening 221 of the threaded portion 22 by way of a connecting piece 51, the outer form of which is conical. To connect and fix the conveying device 5 on the attachment part 2, a connection element 50 in the form of a union nut engages the threads 220 on the threaded portion 22 in a screwing manner via threads 500 on the inside of the connection element 50 such that once the connection element 50 has been screwed onto the threaded portion 22, the conveying device 5 is connected to the attachment part 2.

Figure 8:
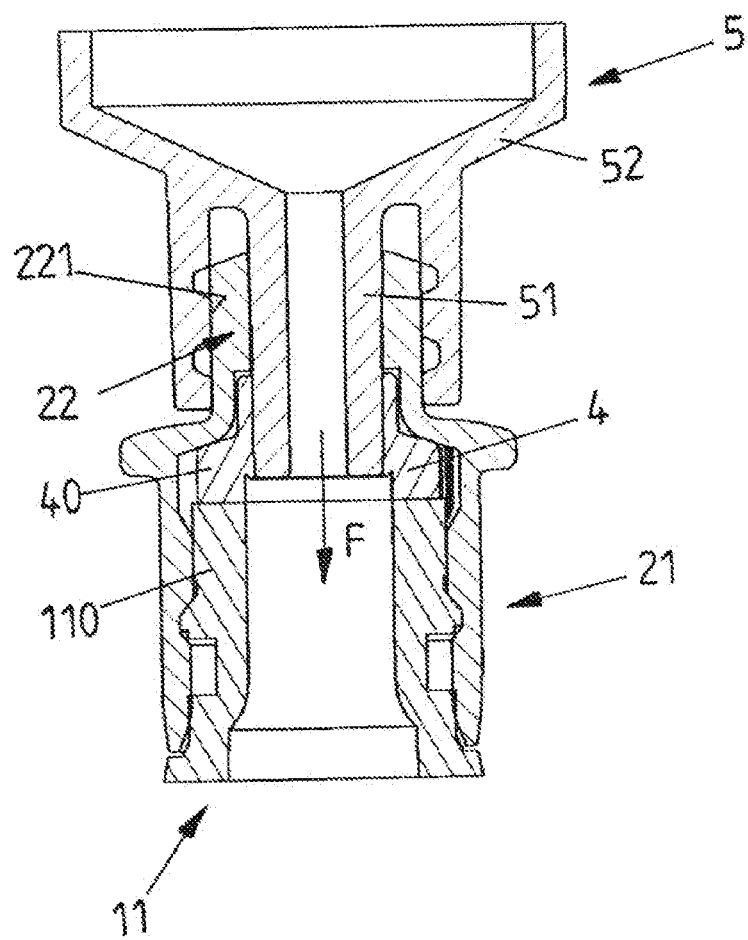
FIG. 8 shows a schematic view of the attachment part with a sealing element arranged therein after attachment of a conveying device in the form of a syringe.

When inserting the connecting piece 51 into the opening 221 of the threaded portion 22 and when screwing the connection element 50 in the form of the union nut onto the threaded portion 22, the connecting piece 51 moves into contact with the sealing head 41 of the sealing element 4 and penetrates it by the connecting piece 51 piercing the slot opening 410 and urging the sealing head 41, as is shown schematically in FIG. 8, radially aside. In this connection, the body 40 is also deformed by being radially widened in the second receiving portion 213.

In the position attached to the attachment part 2, the conveying device 5 penetrates the sealing head 41 of the sealing element 4 preferably entirely by way of its connecting piece 51, as is shown in FIG. 8, such that a flow F between the conveying device 5 and the container 1 is created, the opening width of which flow is not impaired by the sealing element 4.

With the conveying device 5 attached, the connecting piece 51, the form of which is realized in a conical manner, bears flatly against the correspondingly conically formed opening 221 of the threaded portion 22 such that it seals the transition between the conveying device 5 and the attachment part 2.

The sealing element 4 can be produced from a thermoplastic elastomer and can preferably comprise a Shore Hardness of between 25 and 70, for example of between 30 and 60. Because the sealing element 4 is configured in a comparatively rigid manner in said configuration, the conveying device 5 can urge the sealing element 4 efficiently radially aside by way of its connecting piece 51, in particular without the sealing element 4 stretching axially. The greater degree of hardness of the sealing element 4—compared to sealing elements used hitherto—can consequently facilitate the attaching of the conveying device 5 to the attachment part 2 and improve the creating of a flow F with a large flow diameter. In an alternative embodiment, the sealing element 4 can be produced from polyisoprene.

After conveying a medical liquid out of a syringe body 52 of the syringe 5 into the container 1, the conveying device 5 can be removed from the attachment part 2 again by the connection element 50 being released and the conveying device 5 removed from the attachment part 2. This means that the connecting piece 51 is disengaged from the slot opening 410, as a result of which the slot opening 410 closes again automatically and the sealing element 4 consequently returns into its initial state.

Figure 9:
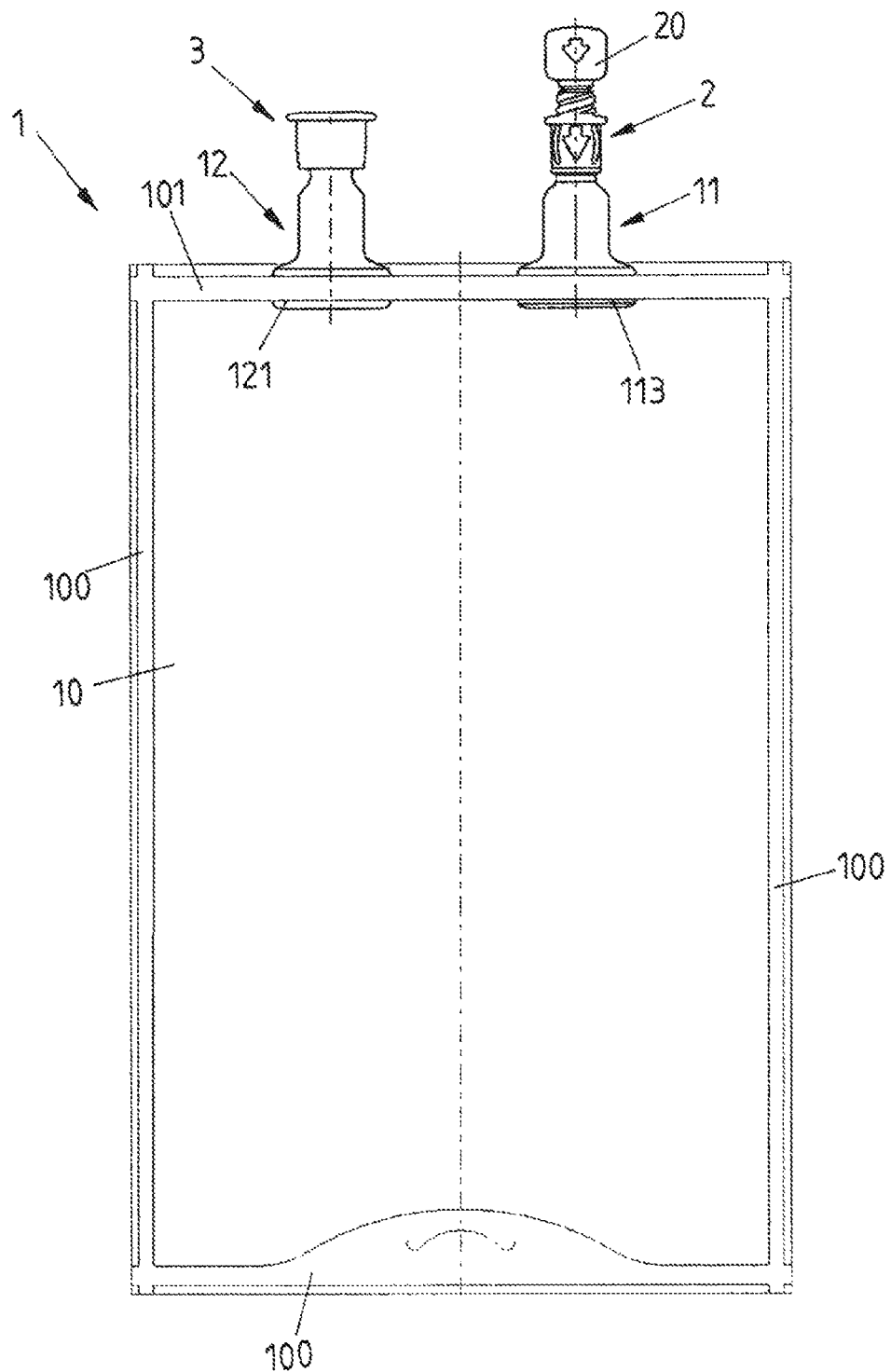
FIG. 9 shows a view of a further exemplary embodiment of a container in the form of a pouch having connection pieces which are arranged thereon and are closed by attachment parts.
Figure 10:
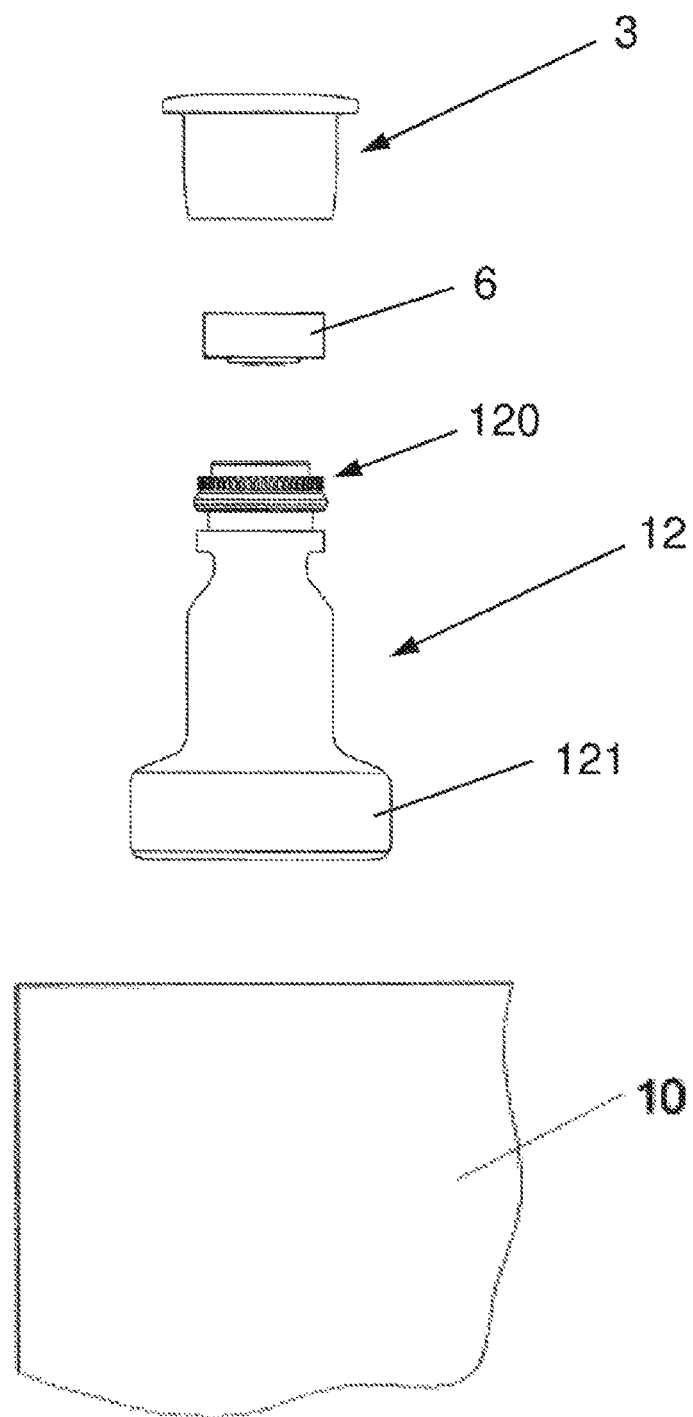
FIG. 10 shows an exploded view of a connection piece with an attachment part which is to be attached thereto in the form of a blind cap.

A further exemplary embodiment of a container 1 is shown in FIGS. 9 and 10.

In the case of the exemplary embodiment according to FIGS. 9 and 10, the container 1 is once again configured as a flexible pouch which is formed from flexible foils. The foils are welded together by means of weld seams 100, 101, connection pieces 11, 12 of two connectors being inserted with portions 113, 121 between the foils of the pouch and being welded with the foils in a liquid-tight manner by means of an upper weld seam 101.

Two connectors, via which access points to the container 1 are created, are provided by means of the connection pieces 11, 12.

In the case of the exemplary embodiment shown, the one connection piece 11 is connected to an attachment part 2, as has been described previously by way of the exemplary embodiment according to FIGS. 2A, 2B to 5. With reference to said connector, reference is consequently to be made entirely to what has previously been described.

The other connection piece 12, in contrast, in the case of the exemplary embodiment, is connected to an attachment part 3 in the form of a so-called blind cap, by means of which the connection piece 12, when the container 1 is used subsequently, is fixedly closed such that a user cannot easily access the container 1 by means of the connection piece 12.

The container 1 of the exemplary embodiment according to FIGS. 9 and 10 can be used, in particular, for dialysis and/or transfusion. During production of the pouch, it is filled by means of the connection piece 12, the blind cap 3 being attached to the connection piece 12 and the connection piece 12 consequently being closed directly after filling. In subsequent operation, the container 1 can then be accessed by means of the other connection piece 11 in order to remove liquid out of the container 1 or to feed it to the container 1.

The connector, which is formed by the blind cap 3 and the connection piece 12, is shown in an exploded view in FIG. 10. The connection piece 12 comprises a head 120, to which the blind cap 3 can be attached for closing the connection piece 12. A sealing element 6, which ensures a liquid-tight closure of the connection piece 12 and is received in the interior of the blind cap 3, is used in this connection between the blind cap 3 and the head 120 of the connection piece 12. With the blind cap 3 attached, the sealing element 6 is held in a clamping manner between the blind cap 3 and the head 120 such that the connection piece 12 is closed in a liquid-tight manner in this way.

The blind cap 3 serves for the purpose of preventing the use of the connector, which is provided by the connection piece 12, when the container 1 is used subsequently. The blind cap 3 cannot easily be removed by a user and is to remain on the connection piece 12 when the container 1 is used subsequently.

When the container 1 is used subsequently, the connection piece 11 is able to be accessed, in contrast, by the break-off piece 20 being broken off in exactly the same way as has been described previously. A conveying device 5, for example in the form of a syringe or a pump, for example a transfusion pump, can be attached to the attachment part 2 in order to fill liquid into the container 1 or to remove it out of the container 1.

To produce the container 1, first of all the flexible foils, which realize the container 1, are rolled out, laid one on top of the other and are, for example, printed. The weld seams 100 are then applied at the sides and at the lower edge of the container 1 such that the foils are tightly connected together at their side edges and at the bottom. The foils are then cut such that the pouch form shown in FIG. 9 is produced.

An opening is then applied in the region of the lower weld seam 100 as suspending means for the container 1.

The foils of the container 1 which are laid one on top of the other are then separated from one another at their upper edge, and the connection pieces 11, 12 are inserted with their portions 113, 121 between the foils. The connection piece 11, in this connection, is inserted with the attachment part 2 attached thereto. The connection piece 12, in contrast, is set between the foils without a blind cap 3.

If the connection pieces 11, 12 have been inserted between the foils, the upper weld seam 101 is applied in order to weld the foils together and to the connection pieces 11, 12 in this way. The pouch interior is closed in a liquid-tight manner in this way. Access points are provided by means of the connection pieces 11, 12.

The container 1 is then filled by means of the connection piece 12, for example with a saline solution or another medical liquid. Once the filling has been completed, the blind cap 3 is attached to the connection piece 12 with the sealing element 6 in order to close the connection piece 12 in this way. Because the attachment part 2 is also attached to the other connection piece 11, the container 1 is consequently closed in a liquid-tight manner.

In order to deliver the container 1 for further use, the container 1 is then shrink-wrapped into an additional wrapping by the container 1 being placed between foils and said foils being welded together.

The container 1, in the shrink-wrapped form, can then be sterilized, for example, and, for example, packed in a box.

For actual use, for example in a hospital, the container 1 is then removed out of the box and the foil wrapping is removed by pulling off the foils. The container 1 can be accessed via the connector of the connection piece 11 which provides a Luer Lock port in order, for example, to remove liquid out of the container 1 so as to flush the transfusion set and/or to infuse a patient.

The concept underlying the invention is not limited to the previously depicted exemplary embodiments, but can also be realized, in principle, with completely different embodiments.

In particular, the present invention can also be used in the case of other containers in the form of ampoules or bottles or the like.

In principle, such a container can comprise one or multiple connection pieces with one or multiple similar or different attachment parts to be arranged thereon.

LIST OF REFERENCES

1 Pouch
10 Pouch body
100, 101 Weld seam
11, 12 Connection piece
110 Head
111 Toothing
112 Positive locking element (ring projection)
113 Widened portion
121 Widened portion
2 Attachment part
20 Break-off part
200 Predetermined breaking point
201 Grip element
21 Connection portion
210 Latching engagement
211 Receiving portion
212 Toothing
213 Receiving portion
214 Toothing
215 Receiving portion
216 Opening
217 First step
218 Second step
219 Third step
22 Threaded portion
220 Thread
221 Opening
223 Lead-in chamfer
224 Projection
3 Attachment part
30 Break-off piece
4 Sealing element
40 Body
41 Sealing head
410 Slot opening
411 Side
42 Interior
43 Annulus
44 Groove or indentation
5 Conveying device (syringe)
50 Connection element
500 Thread
51 Connecting piece (syringe cone)
52 Syringe body
6 Sealing element
D1, D2, D3 Diameter
E Insertion direction
F Flow direction

The invention claimed is:

1. A container for a medical liquid, the container having
    a connection piece by means of which a medical liquid is conveyable into the container or out of the container,
    an attachment part that is attachable to the connection piece and is connectable to a conveying device for conveying a medical liquid into the container or out of the container, and
    a sealing element for sealing a transition between the connection piece and the attachment part, wherein the sealing element comprises a slot opening that, with the conveying device not attached to the attachment part, is closed against a passage of liquid and, as a result of attaching the conveying device to the attachment part, is to be opened in such a manner that a medical liquid is conveyable through the slot opening, wherein
    the attachment part comprises a connecting portion with an opening into which the connection piece is insertable along an insertion direction for connection to the attachment part and the opening comprises a first receiving portion and a second receiving portion that connects axially thereto along the insertion direction, wherein, with the attachment part attached to the connection piece, the first receiving portion receives a head of the connection piece and the second receiving portion receives a portion of the sealing element, wherein the first receiving portion comprises a first diameter and the second receiving portion comprises a second diameter, wherein the first diameter is smaller than the second diameter and the sealing element, with the conveying device not attached to the attachment part, is received in the second receiving portion with radial play,
    wherein the sealing element comprises a sealing head and a cylindrical body, and
    wherein the cylindrical body is not clamped by the attachment part.

2. The container as claimed in claim 1, wherein the sealing element is produced from a thermoplastic elastomer that comprises a Shore Hardness A of between 25 and 70.

3. The container as claimed in claim 1, wherein the sealing element is produced from polyisoprene.

4. The container as claimed in claim 1, wherein the second diameter of the second receiving portion is greater than the first diameter of the first receiving portion by between 0.2 mm and 1.5 mm.

5. The container as claimed in claim 1, wherein the first receiving portion and the second receiving portion each comprise an inner toothing that extends around the insertion direction.

6. The container as claimed in claim 1, wherein the sealing element comprises a body and a sealing head, wherein the body is clamped between the connection piece and the attachment part with the attachment part attached to the connection piece, wherein the sealing head connects to the body, and wherein the sealing head comprises the slot opening.

7. The container as claimed in claim 6, wherein the body of the sealing element comprises an outer diameter of between 6 mm and 10 mm and the sealing head, which connects to the body, comprises an outer diameter of between 4 mm and 7 mm.

8. The container as claimed in claim 6, wherein the sealing head is flat, convex, or concave manner on a side remote from the body.

9. The container as claimed in claim 6, wherein the body of the sealing element comprises a cylindrical bore with a diameter that, with the conveying device not attached to the attachment part, is closed by the sealing head against a passage of liquid.

10. The container as claimed in claim 1, wherein the attachment part comprises a threaded portion and a break-off piece, wherein the threaded portion comprises a threaded-portion opening and a thread, wherein the break-off piece is connected to the threaded portion, wherein the threaded portion forms a threaded connection with the conveying device, wherein the break-off piece, when connected to the threaded portion, closes the threaded-portion opening, and wherein, when the break-off piece is removed from the threaded portion, the break-off piece opens the threaded-portion opening.

11. The container as claimed in claim 10, wherein the threaded portion and the break-off piece are formed in one piece, wherein a predetermined breaking point for breaking-off the break-off piece from the threaded portion is arranged between the threaded portion and the break-off piece.

12. A sealing element for a container as claimed in claim 1, wherein the sealing element comprises a body with an outer diameter of between 6 mm and 10 mm and a sealing head which connects to the body with an outer diameter of between 4 mm and 7 mm.

13. An arrangement having a container having a sealing element as claimed in claim 12, which is inserted in a connector with radial play, and a conveying device which comprises a connecting piece for the attachment to the attachment part, wherein, with the conveying device attached to the attachment part, the connecting piece penetrates the slot opening of the sealing element.

14. An arrangement having a container as claimed in claim 1, the arrangement having a connector that is inserted in a connector with radial play and a conveying device that comprises a connecting piece for the attachment to the attachment part, wherein, with the conveying device attached to the attachment part, the connecting piece penetrates the slot opening of the sealing element.

15. The arrangement as claimed in claim 14, wherein the conveying device has an opening cross section through which liquid is transported and wherein, when attached to the attachment part, the conveying device extends through the slot opening and at least 80% of the opening cross section of the conveying device remains uncovered by the sealing element.

16. The container of claim 1, wherein the second receiving portion of the opening is defined by an outer wall and the sealing element does not contact the outer wall with the conveying device not attached.

17. The container of claim 16, wherein, with the conveying device not attached, there exists a space between the outer wall of the second receiving portion and the sealing element.

18. The container of claim 16, wherein the sealing element is radially widened in the second receiving portion with the conveying device attached.

19. The container of claim 18, wherein the sealing element contacts the outer wall with the conveying device attached.

20. A connector for a container for a medical liquid, the connector having a connection piece, through which a medical liquid is conveyable, an attachment part which is attachable to the connection piece and is connectable to a conveying device for conveying a medical liquid through the connection piece, and a sealing element for sealing a transition between the connection piece and the attachment part, wherein the sealing element comprises a slot opening which, with the conveying device not attached to the attachment part, is closed against a passage of liquid and, as a result of attaching the conveying device to the attachment part, is to be opened in such a manner that a medical liquid is conveyable through the slot opening, wherein the attachment part comprises a connecting portion with an opening into which the connection piece is insertable along an insertion direction for connection to the attachment part and the opening comprises a first receiving portion and a second receiving portion which connects axially thereto along the insertion direction, wherein, with the attachment part attached to the connection piece, the first receiving portion receives a head of the connection piece and the second receiving portion receives a portion of the sealing element wherein the first receiving portion comprises a first diameter and the second receiving portion comprises a second diameter, wherein the first diameter is smaller than the second diameter and the sealing element, with the conveying device not attached to the attachment part, is received in the second receiving portion with radial play wherein the sealing element comprises a sealing head and a cylindrical body, and wherein the cylindrical body is not clamped by the attachment part.

21. A sealing element for a connector as claimed in claim 20, wherein the sealing element comprises a body with an outer diameter of between 6 mm and 10 mm and a sealing head, which connects to the body, with an outer diameter of between 4 mm and 7 mm.

* * * * *